United States Patent
Singh et al.

(10) Patent No.: US 9,974,567 B2
(45) Date of Patent: *May 22, 2018

(54) GENERAL UTERINE MANIPULATOR AND SYSTEM

(71) Applicants: Jiwan Steven Singh, Woodvale (AU); Jai Singh, Woodvale (AU)

(72) Inventors: Jiwan Steven Singh, Woodvale (AU); Jai Singh, Woodvale (AU)

(*) Notice: Subject to any disclaimer, the term of this patent is extended or adjusted under 35 U.S.C. 154(b) by 11 days.

This patent is subject to a terminal disclaimer.

(21) Appl. No.: 15/246,140

(22) Filed: Aug. 24, 2016

(65) Prior Publication Data

US 2017/0135727 A1    May 18, 2017

Related U.S. Application Data

(63) Continuation of application No. 14/007,820, filed as application No. PCT/AU2012/000332 on Mar. 30, 2012, now Pat. No. 9,451,985.

(Continued)

(51) Int. Cl.
*A61B 17/42* (2006.01)
*A61B 17/00* (2006.01)

(52) U.S. Cl.
CPC .... *A61B 17/4241* (2013.01); *A61B 17/00234* (2013.01); *A61B 2017/4216* (2013.01)

(58) Field of Classification Search
CPC ............... A61B 17/4241; A61B 17/42; A61B 2017/4216; A61B 2017/4225; A61B 10/0291
See application file for complete search history.

(56) References Cited

U.S. PATENT DOCUMENTS 2,191,721 A    2/1940    Milarch
2,201,372 A    5/1940    Miller
(Continued)

FOREIGN PATENT DOCUMENTS

AU    773391    5/2004
AU    2011101651 A4    2/2012
(Continued)

OTHER PUBLICATIONS

SecuFix Uterus Manipulator, 4 pages, www.richard-wolf.com. The "publication date" of this reference is not readily available. Applicant requests that the Examiner review the reference as prior art. Applicant reserves the right to disqualify the reference as prior art if needed.

(Continued)

*Primary Examiner* — Jonathan Miles
(74) *Attorney, Agent, or Firm* — Knobbe, Martens, Olson & Bear, LLP

(57) ABSTRACT

A general uterine manipulator 10 incorporates an elongated hollow tube 12 defining an internal passage 14. Tube 12 has opposite first and second ends 16 and 18, formed with internal threads T1 and T2; and a smooth continuous outer surface 20 of constant outer diameter. A first fitting comprising a tail screw 22 is screwed into thread T1 and a second fitting cervical screw 24 is screwed in thread T2. An inner manipulator rod 26 extends through the first fitting 22, tube 12, and second fitting 24. A range of alternate first and second fitting is provided. A forceps holder 70 is attachable to the tube 12 between ends 16 and 18. The manipulator 10 may also support a cervical funnel 90 and a plug 92.

20 Claims, 11 Drawing Sheets

Related U.S. Application Data

(60) Provisional application No. 61/472,705, filed on Apr. 7, 2011.

(56) References Cited

U.S. PATENT DOCUMENTS

| | | | |
|---|---|---|---|
| 2,400,251 | A | 5/1946 | Nagel |
| 2,470,308 | A | 5/1949 | Haddican |
| 2,636,598 | A | 4/1953 | Hopgood |
| 2,707,471 | A | 5/1955 | Koff |
| 3,465,529 | A | 9/1969 | Helle |
| 3,926,192 | A | 12/1975 | Van Maren |
| 4,045,027 | A | 8/1977 | Manska |
| 4,117,847 | A | 10/1978 | Clayton |
| 4,207,872 | A | 6/1980 | Meiri et al. |
| 4,382,445 | A | 5/1983 | Sommers |
| 4,430,076 | A | 2/1984 | Harris |
| 4,573,452 | A | 3/1986 | Greenberg |
| 4,840,613 | A | 6/1989 | Balbierz |
| 4,859,067 | A | 8/1989 | Hoppe et al. |
| 4,863,133 | A | 9/1989 | Bonnell |
| 4,863,174 | A | 9/1989 | Cummings |
| 4,998,924 | A | 3/1991 | Ranford |
| 5,003,146 | A | 3/1991 | Alexander |
| 5,052,998 | A | 10/1991 | Zimmon |
| 5,112,346 | A | 5/1992 | Hiltebrandt et al. |
| 5,138,228 | A | 8/1992 | Thomas et al. |
| 5,156,599 | A | 10/1992 | Ranford et al. |
| 5,167,614 | A | 12/1992 | Tessmann et al. |
| 5,191,888 | A | 3/1993 | Palmer et al. |
| 5,205,831 | A | 4/1993 | Ryan et al. |
| 5,320,613 | A | 6/1994 | Houge et al. |
| 5,338,313 | A | 8/1994 | Mollenauer et al. |
| 5,395,331 | A | 3/1995 | O'Neill et al. |
| 5,425,739 | A | 6/1995 | Jessen |
| 5,472,419 | A | 12/1995 | Bacich |
| 5,487,377 | A | 1/1996 | Smith et al. |
| 5,542,321 | A | 8/1996 | Fuca |
| 5,643,285 | A | 7/1997 | Rowden et al. |
| 5,741,333 | A | 4/1998 | Frid |
| RE35,849 | E | 7/1998 | Soehendra |
| 5,792,165 | A | 8/1998 | Klieman |
| 5,800,514 | A | 9/1998 | Nunez et al. |
| 5,840,077 | A | 12/1998 | Rowden |
| 5,876,383 | A | 3/1999 | Grooters et al. |
| 5,931,820 | A | 8/1999 | Morse |
| 5,947,954 | A | 9/1999 | Bonaldo |
| 5,957,423 | A | 9/1999 | Kronner |
| 6,004,302 | A | 12/1999 | Brierley |
| 6,010,520 | A | 1/2000 | Pattison |
| 6,096,022 | A | 8/2000 | Laymon et al. |
| 6,124,523 | A | 9/2000 | Banas et al. |
| 6,203,532 | B1 | 3/2001 | Wright |
| 6,254,578 | B1 | 7/2001 | Grooters et al. |
| 6,371,981 | B1 | 4/2002 | Yang et al. |
| 6,423,075 | B1 | 7/2002 | Singh et al. |
| 6,516,216 | B1 | 2/2003 | Fontenot et al. |
| 6,517,570 | B1 | 2/2003 | Lau et al. |
| 6,572,593 | B1 | 6/2003 | Daum |
| 6,589,213 | B2 | 7/2003 | Reydel |
| 6,692,504 | B2 | 2/2004 | Kurz et al. |
| 6,758,834 | B2 | 7/2004 | Grooters |
| 6,767,339 | B2 | 7/2004 | Reydel |
| 6,811,547 | B2 | 11/2004 | Wilkinson |
| 6,893,428 | B2 | 5/2005 | Willemstyn |
| 7,044,962 | B2 | 5/2006 | Elliott |
| 7,195,641 | B2 | 3/2007 | Palmaz et al. |
| 7,338,530 | B2 | 3/2008 | Carter et al. |
| 7,811,148 | B2 | 10/2010 | Fridrich |
| 7,811,278 | B2 | 10/2010 | Knipple, Jr. et al. |
| 7,993,328 | B2 | 8/2011 | Whitley |
| 8,042,775 | B1 | 10/2011 | Gallegos |
| 8,052,650 | B2 | 11/2011 | Young et al. |
| 8,287,517 | B2 | 10/2012 | Hanlon et al. |
| 8,298,213 | B2 | 10/2012 | Singh |
| 8,495,809 | B2 | 7/2013 | Valtchev |
| 8,567,754 | B1 | 10/2013 | Gilstad et al. |
| 8,568,423 | B2 | 10/2013 | Boebel et al. |
| 8,574,221 | B2 | 11/2013 | Deeds |
| 8,603,105 | B2 | 12/2013 | Sauer |
| 8,623,070 | B2 | 1/2014 | Bales et al. |
| 8,647,325 | B2 | 2/2014 | Charlez |
| 8,647,326 | B2 | 2/2014 | Solomon et al. |
| 8,647,349 | B2 | 2/2014 | Gruber et al. |
| 8,663,239 | B2 | 3/2014 | Hess |
| 8,709,362 | B2 | 4/2014 | Leventhal et al. |
| 8,740,916 | B2 | 6/2014 | Blair et al. |
| 8,770,200 | B2 | 7/2014 | Ahluwalia |
| 8,876,800 | B2 | 11/2014 | Kaufmann et al. |
| 8,876,886 | B2 | 11/2014 | Kaufmann et al. |
| 9,101,390 | B2 | 8/2015 | Singh et al. |
| 9,451,985 | B2 | 9/2016 | Singh et al. |
| 9,532,837 | B2 | 1/2017 | Singh et al. |
| 2002/0095160 | A1 | 7/2002 | Bonutti |
| 2002/0120252 | A1 | 8/2002 | Brock et al. |
| 2004/0097961 | A1 | 5/2004 | Burbank et al. |
| 2004/0204720 | A1 | 10/2004 | Harrington et al. |
| 2004/0236285 | A1 | 11/2004 | Fisher et al. |
| 2005/0085827 | A1 | 4/2005 | G. et al. |
| 2005/0277948 | A1 | 12/2005 | Cedars et al. |
| 2007/0135819 | A1 | 6/2007 | Spiritos et al. |
| 2008/0039865 | A1 | 2/2008 | Shaher et al. |
| 2009/0048609 | A1 | 2/2009 | Atiomo et al. |
| 2009/0062839 | A1 | 3/2009 | Kurrus |
| 2010/0160928 | A1 | 6/2010 | Navas |
| 2010/0274260 | A1 | 10/2010 | D'Arpiany et al. |
| 2011/0282368 | A1 | 11/2011 | Swayze et al. |
| 2011/0306829 | A1 | 12/2011 | Sharp et al. |
| 2012/0109124 | A1 | 5/2012 | Morozov |
| 2012/0143209 | A1 | 6/2012 | Brecheen et al. |
| 2012/0143210 | A1 | 6/2012 | Brecheen et al. |
| 2013/0066328 | A1 | 3/2013 | Singh et al. |
| 2013/0197536 | A1 | 8/2013 | Singh et al. |
| 2014/0100595 | A1 | 4/2014 | Morgenstern Lopez et al. |
| 2014/0135587 | A1 | 5/2014 | Hess |
| 2014/0276916 | A1 | 9/2014 | Ahluwalia et al. |
| 2014/0303641 | A1 | 10/2014 | Boebel et al. |
| 2016/0081717 | A1 | 3/2016 | Singh et al. |

FOREIGN PATENT DOCUMENTS

| | | |
|---|---|---|
| AU | 2007335226 | 9/2012 |
| CA | 2778976 | 8/2012 |
| CN | 201005764 | 1/2008 |
| DE | 10208508 | 1/2003 |
| EP | 0400458 | 12/1990 |
| JP | 2006-122674 | 10/2005 |
| JP | 2009-273891 | 11/2009 |
| JP | 2011-104399 | 6/2011 |
| KR | 10-2001-0052102 A | 6/2001 |
| WO | WO 2008/074054 | 6/2008 |
| WO | WO 2008/136024 | 9/2008 |
| WO | WO 2010/151429 | 12/2010 |
| WO | WO 2011/140604 | 9/2011 |
| WO | WO 2012/135893 | 10/2012 |
| WO | WO 2013/102235 | 7/2013 |
| WO | WO 2013/159019 | 10/2013 |
| WO | WO 2014/047554 | 3/2014 |

OTHER PUBLICATIONS

Cooper Surgical, "Uterine Positioning SystemTM Facilitates accurate and secure uterine placement," Brochure, revision Dec. 2008, in 5 pages, Trumbull, CT.

Surgitools, Instructions for Use: Singh MultiGuide ARC, Apr. 30, 2013.

International Preliminary Report on Patentability for PCT Application No. PCT/AU2012/000332, dated Feb. 27, 2013.

International Search Report and Written Opinion, International Application No. PCT/AU2012/000332, International Filing Date, Mar. 30, 2012, dated May 17, 2012.

International Search Report and Written Opinion for PCT Application No. PCT/US2013/061180, dated Dec. 17, 2013.

(56) References Cited

OTHER PUBLICATIONS

International Search Report and Written Opinion for PCT/US2013/037417, dated Jul. 29, 2013.
Ob.Gyn.News, "Kronner non-Pneumatic Scope/Instrument Holder for laparoscopic and other endoscopic surgery," updated Mar. 16, 2013, in 2 pages, product.zone.obgynnews.com.
R. Kronner, MD FACS, "The Kronner Side-Kick: A Perineal Instrument Holder," manual in 13 pages, Kronner Medical, Roseburg, Oregon.
Stryker, "Give Yourself a Hand," Stryker Endoscopy Brochure, in 2 pages, 2006, Stryker, San Jose, CA.

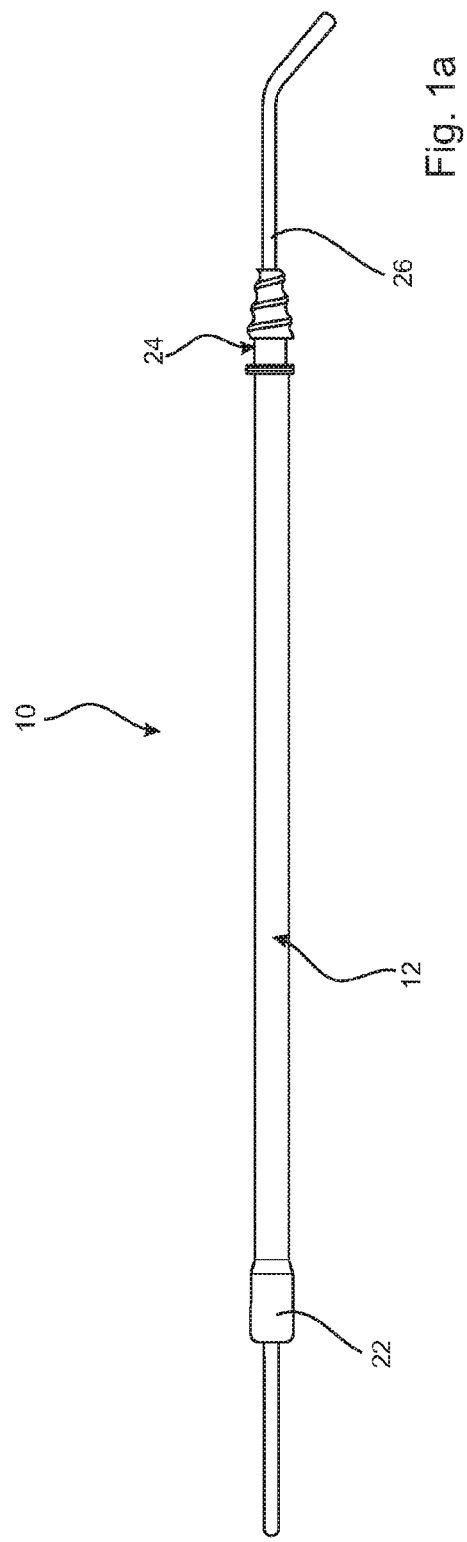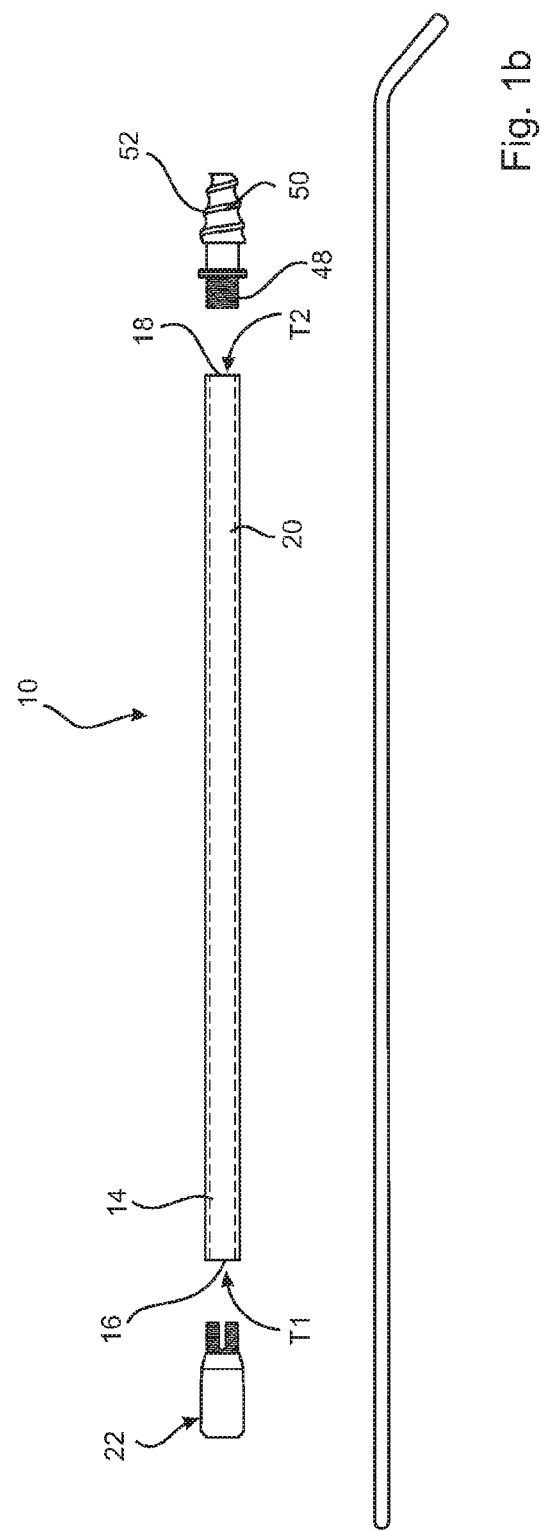

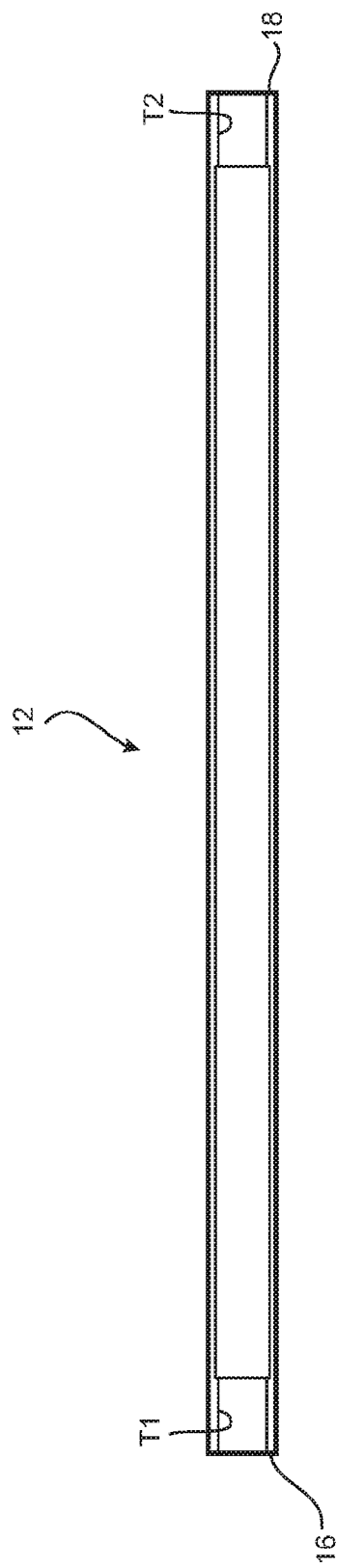

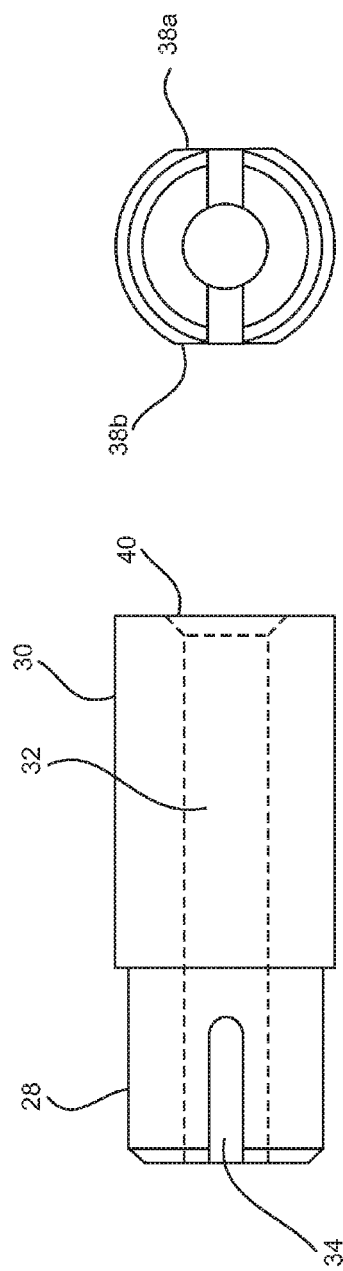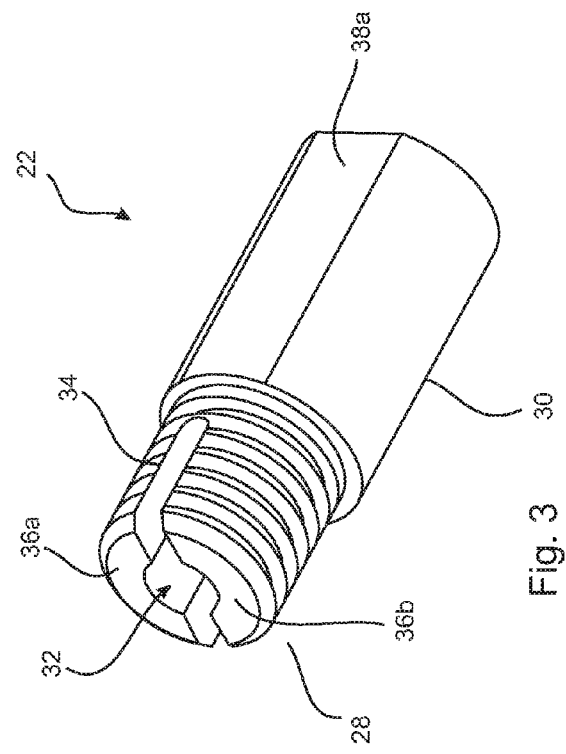

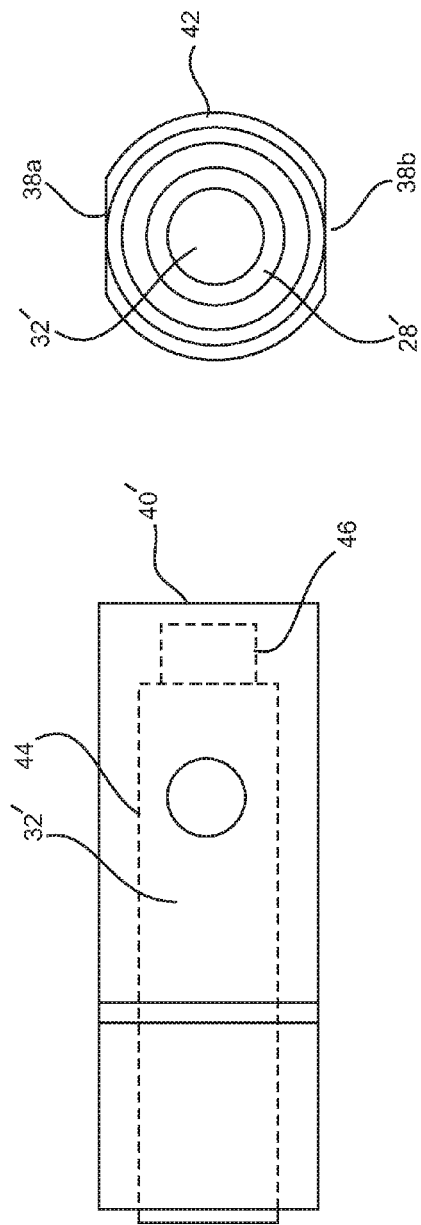
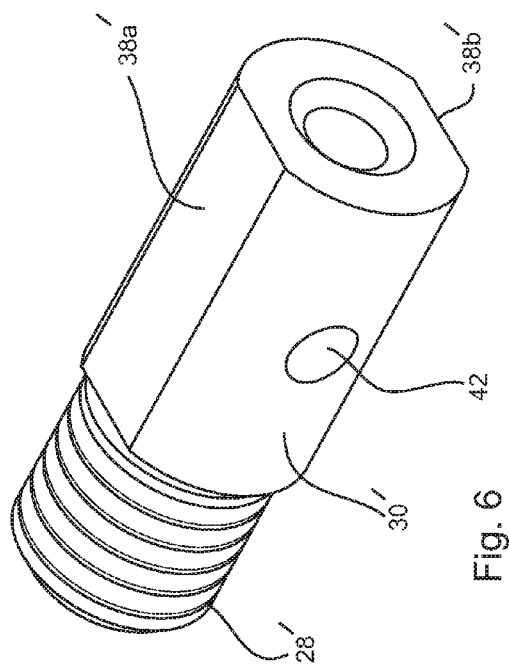

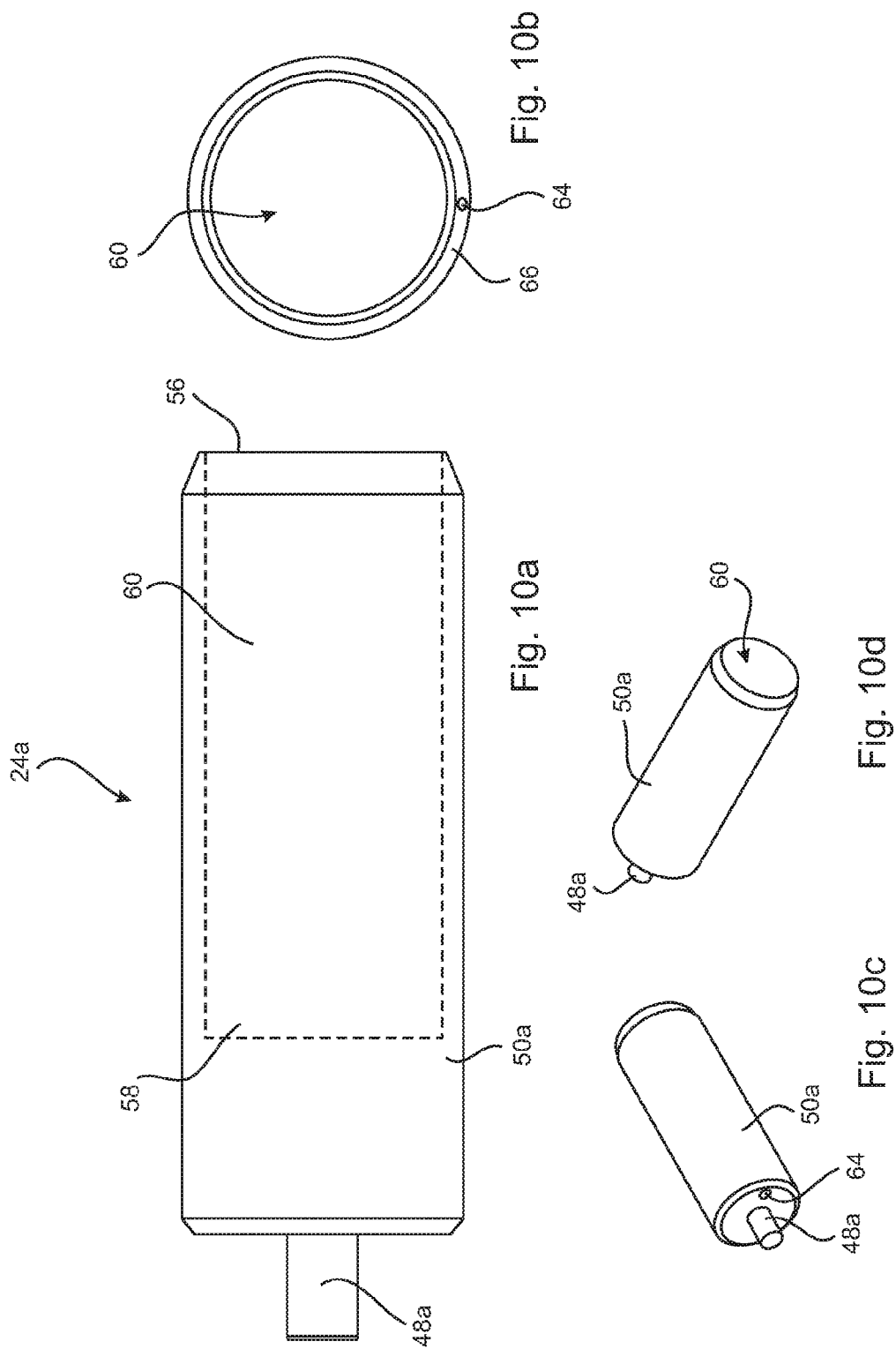

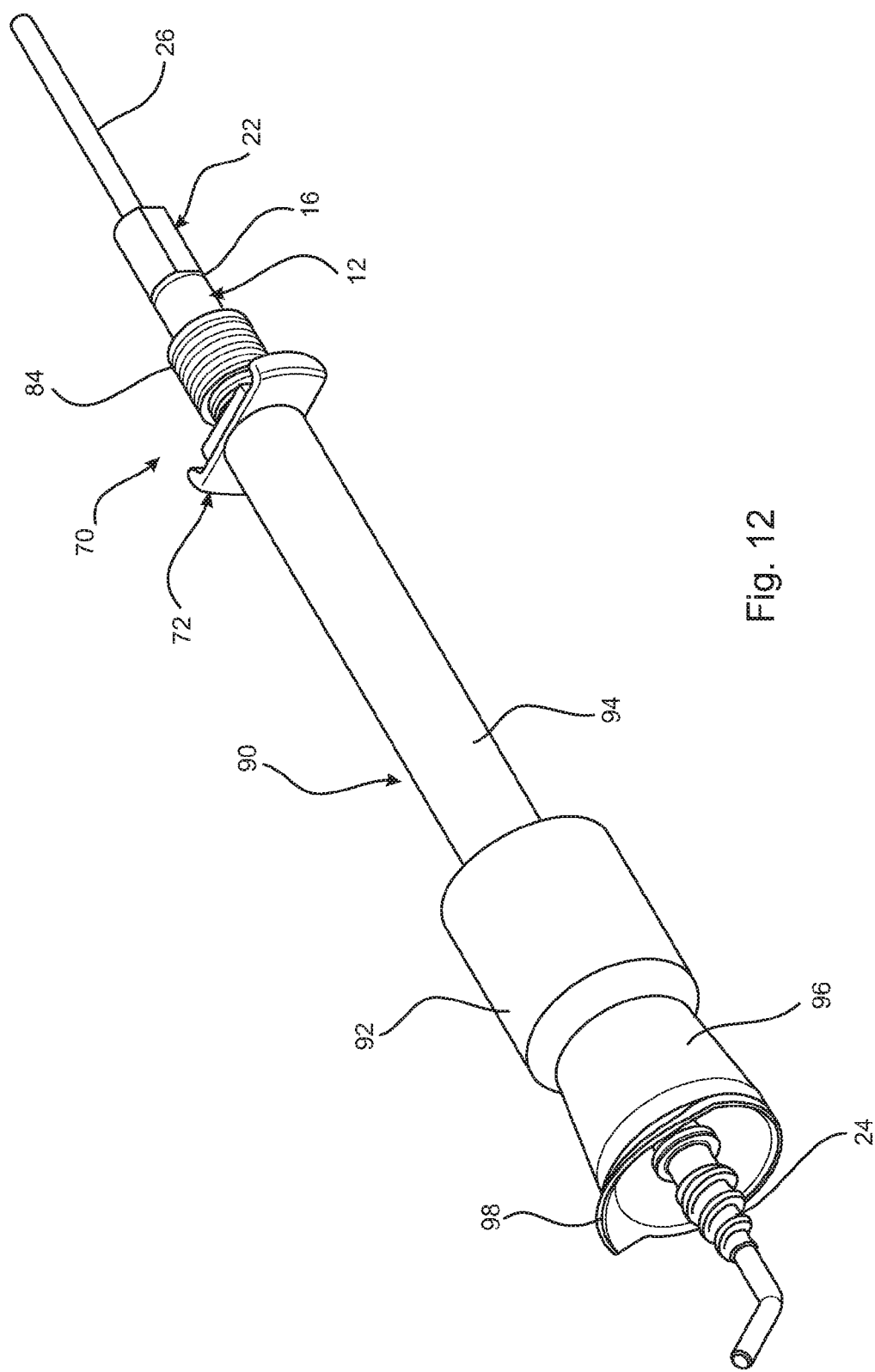

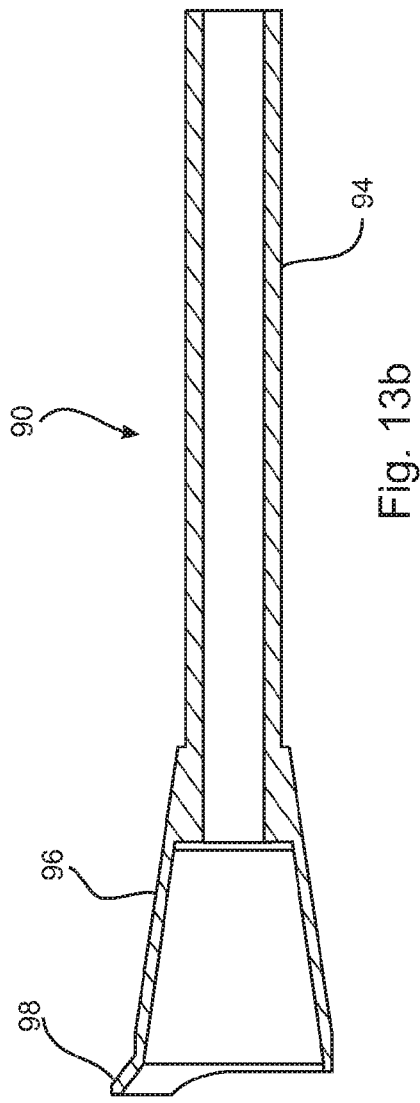
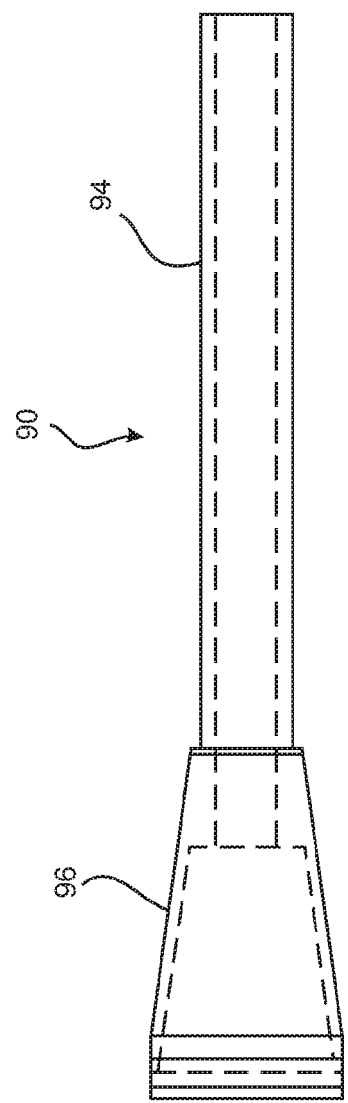
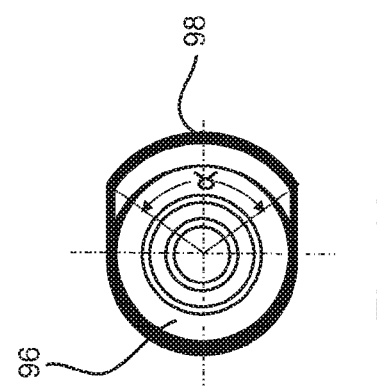

GENERAL UTERINE MANIPULATOR AND SYSTEM

INCORPORATION BY REFERENCE TO ANY PRIORITY APPLICATIONS

This application is a Continuation of U.S. Patent Application Ser. No. 14/007,820, titled GENERAL UTERINE MANIPULATOR AND SYSTEM, filed Oct. 31, 2013, which is a National Stage of PCT Application No. PCT/AU2012/000332, titled GENERAL UTERINE MANIPULATOR AND SYSTEM, filed Mar. 30, 2012, which claims the benefit of U.S. Provisional Patent Application Ser. No. 61/472,705, titled GENERA UTERINE MANIPULATOR AND SYSTEM, filed Apr. 7, 2011. Each of the foregoing applications is hereby incorporated by reference herein in its entirety.

FIELD OF THE INVENTION

The present invention relates to a general uterine manipulator and system which may be used in general surgery, gynaecological or non-surgical procedures.

BACKGROUND OF THE INVENTION

The present inventor has invented numerous medical instruments which are currently in use in surgical and non-surgical procedures. One such instrument is described in International publication no. WO 2008/074054 which is used in various procedures including total laparoscopic hysterectomy. The instrument described in this publication comprises a tube provided with an integral funnel at one end and through which a uterine cannula can be inserted. Both the tube and the cannula are provided with longitudinal slots or cut outs that aid in visualising the rotational position of a distal end of the instrument when inserted into the vagina and also aid in gripping of the instrument.

The success and efficacy of the above described and other instruments developed by the present inventor together with the need for improved and more versatile instruments have lead to the present invention.

SUMMARY OF THE INVENTION

According to one aspect of the present invention there is provided a general uterine manipulator comprising:

an elongated hollow tube defining an internal passage and having opposite first and second ends;

a smooth continuous outer surface of constant outer diameter extending between the first and second ends; and, internal first and second screw threads formed in the elongated hollow tube, the first screw thread being formed at the first end and the second screw thread being formed at the second end.

The general uterine manipulator may comprise a first fitting having a screw thread arranged to engage the first screw thread, the first fitting also having an axial through hole and configured to receive an inner manipulator shaft.

In some embodiments the first fitting is configured to apply increasing clamping force on a received inner manipulator when the first fitting a screw further into the first end.

The general uterine manipulator may comprise a hydrotubation port in fluid communication with the internal passage wherein a fluid injected into or through the hydrotubation port is able to flow into the internal passage.

In some embodiments the hydrotubation port is formed in the elongated hollow tube at a location near the first end and beyond the first screw thread.

In some embodiments the hydrotubation port is formed in the first fitting and is in fluid communication with the axial through hole.

The axial through hole may comprise a first length which opens onto an end of the first fitting distant the screw thread of the first fitting, and a second contiguous length wherein the first length has a first internal diameter and the second length has a second internal diameter which is greater than the first internal diameter; and wherein the hydrotubation port opens onto the second length of the axial through hole.

The general uterine manipulator may comprise a second fitting having a threaded portion provided with a screw thread configured to engage the second internal thread on the elongated hollow tube and a body portion extending co-linearly from the threaded portion.

In some embodiments the body portion comprises a tubular member which is open at one end distal the threaded portion and is closed at an end near to the threaded portion to form a cavity.

In some embodiments the tubular member comprises a circumferential wall and at least one internal passage formed in the circumferential wall, the or each internal passage opening onto axially opposite ends of the circumferential wall.

In some embodiments the body portion comprises a conically shaped portion with decreasing outer diameter in a taper direction being away from the threaded portion and wherein the conically shaped portion is provided with an external coarse screw thread.

In some embodiments the second fitting is provided with an axial through hole.

The general uterine manipulator may comprise an inner manipulator shaft, the shaft capable of being received in the axial through hole of the first fitting and the axial through hole of the second fitting and extending through the internal passage.

In some embodiments a crest of the coarse screw thread is provided with a flattened surface wherein a line on the flattened surface is inclined relative to a central axis of the coarse screw thread in the taper direction.

In some embodiments the coarse screw thread is a ball screw thread.

In some embodiments the general uterine manipulator comprising a forceps holder supported on the elongated hollow tube and configured to be releasably lockable in a plurality of positions along the elongated hollow tube.

In some embodiments the forceps holder comprises a first component seated on the elongated hollow tube and provided with a detent for gripping a finger hole of the forceps.

In some embodiments the forceps holder comprises a locking nut engagable with the first component and arranged to releasably lock the first component in a fixed position along the elongated hollow tube when rotated in a first direction, and to release the second component to allow sliding motion along the elongated hollow tube when rotated in an opposite direction.

In a second aspect there is provided general uterine manipulator comprising:

an elongated hollow tube defining an internal passage and having opposite first and second ends;

a smooth continuous outer surface of constant outer diameter extending between the first and second ends;

internal first and second screw threads formed in the elongated hollow tube, the first screw thread being formed at the first end and the second screw thread being formed at the second end a first fitting having a screw thread arranged to engage the first screw thread, the first fitting also having an axial through hole;

a second fitting having a threaded portion provided with a screw thread configured to engage the second internal thread on the elongated hollow tube and a body portion extending co-linearly from the threaded portion; and, an inner manipulator shaft arranged to extend through the axial through hole, the internal passage and the second fitting, the inner manipulator shaft having one end which is bent and protrudes from the second fitting.

In one embodiment the general uterine manipulator comprises a resistance mechanism enabling the axial and rotational position of the inner manipulator shaft to substantially held in the absence of adjustment by a user of the manipulator.

In one embodiment the resistance mechanism comprises clamp shells incorporated in the first fitting.

In one embodiment the resistance mechanism comprises a bend in a portion of the inner manipulator shaft within the internal passage the bend being to an extent that the inner manipulator shaft bears against an inside surface of the tube.

In one embodiment the general uterine manipulator comprises a hydrotubation port formed in the first fitting and in fluid communication with the axial through hole wherein a fluid injected into or through the hydrotubation port is able to flow into the internal passage. In this embodiment the axial through hole comprises a first length which opens onto an end of the first fitting distant the screw thread of the first fitting, and a second contiguous length wherein the first length has a first internal diameter and the second length has a second internal diameter which is greater than the first internal diameter; and the hydrotubation port opens onto the second length of the axial through hole.

In one embodiment the second fitting comprises a threaded portion provided with a screw thread configured to engage the second internal thread on the elongated hollow tube and a body portion extending co-linearly from the threaded portion, the body portion having a frusto-conical shape with decreasing outer diameter in a direction away from the threaded portion and on which is provided an external coarse screw thread.

In one embodiment the general uterine manipulator comprises a forceps holder supported on the elongated hollow tube and configured to be releasably lockable in a plurality of positions along the elongated hollow tube.

In one embodiment the forceps holder comprises a first component seated on the elongated hollow tube and provided with a detent for gripping a handle of the forceps.

In one embodiment the forceps holder comprises a locking nut engagable with the first component and arranged to releasably lock the first component in a fixed position along the elongated hollow tube when rotated in a first direction, and to release the second component to allow sliding motion along the elongated hollow tube when rotated in an opposite direction.

In one embodiment the general uterine manipulator comprises a cervical funnel mounted on the tube.

In a third aspect there is provided a general uterine manipulator system comprising:

an elongated hollow tube defining an internal passage and having opposite first and second ends;

a smooth continuous outer surface of constant outer diameter extending between the first and second ends;

internal first and second screw threads formed in the elongated hollow tube, the first screw thread being formed at the first end and the second screw thread being formed at the second end at least one first fitting the or each first fitting having a screw thread arranged to engage the first screw thread, the first fitting also having an axial through hole;

at least one second fitting the or each second fitting having a threaded portion provided with a screw thread configured to engage the second internal thread on the elongated hollow tube and a body portion extending co-linearly from the threaded portion;

wherein the at least one first fitting comprises one or both of: (a) a clamping first fitting configured to apply increasing clamping force on a received inner manipulator when the first fitting a screw further into the first end; and (b) a hydrotubation first fitting which has a hydrotubation port in fluid communication with the internal passage wherein a fluid injected into or through the hydrotubation port is able to flow into the internal passage; and wherein the at least one second fitting comprises one or both of: (c) a cervical second fitting in which its body portion is of a frusto-conical shape with decreasing outer diameter in a direction away from the threaded portion and is provided with an external coarse screw thread; and (d) a tubular second fitting in which its body portion comprises a tubular member which is open at one end distal the threaded portion of the second fitting and is closed at an end near to the threaded portion of the second fitting to form a cavity.

In one embodiment the tubular member of the tubular second fitting comprises a circumferential wall and at least one internal passage formed in the circumferential wall, the or each internal passage opening onto axially opposite ends of the circumferential wall.

In one embodiment the general uterine manipulator system comprises an inner manipulator shaft arranged to extend through the axial through hole, the internal passage and the second fitting when the second fitting is the cervical second fitting, the inner manipulator shaft having one end which is bent and protrudes from the cervical.

In one embodiment the general uterine manipulator system a resistance mechanism enabling the axial and rotational position of the inner manipulator shaft to substantially held in the absence of adjustment by a user.

In one embodiment the general uterine manipulator system a forceps holder supported on the elongated hollow tube and configured to be releasably lockable in a plurality of positions along the elongated hollow tube.

BRIEF DESCRIPTION OF THE DRAWINGS

FIG. 1a is a representation of one embodiment of a general uterine manipulator in accordance with the present invention;

FIG. 1b is a disassembled view of the general uterine manipulator depicted in FIG. 1a;

FIG. 2 is a longitudinal section view of the tube incorporated in the general uterine manipulator shown in FIGS. 1a and 1b;

FIG. 3 is an isometric view of a tail screw incorporated in the general uterine manipulator shown in FIGS. 1a and 1b;

FIG. 4 is a side view of the tail screw shown in FIG. 3;

FIG. 5 is an end view of the tail screw shown in FIG. 3;

FIG. 6 is an isometric view of a second form of tail screw that may be incorporated in the general uterine manipulator shown in FIGS. 1a and 1b;

FIG. 7 is a side view of the tail screw shown in FIG. 6;

FIG. 8 is an end view of the tail screw shown in FIG. 6;

FIG. 9b is a longitudinal section view of the second fitting shown in FIG. 9a;

FIG. 10a is a side view of a second form of setting fitting that may be incorporated in the general uterine manipulator depicted in FIGS. 1a and 1b;

FIG. 10b is an end view of the second fitting shown in FIG. 9a;

FIG. 10c is an isometric view from one end of the second fitting;

FIG. 10d is a isometric view from an opposite angle of the second fitting;

FIG. 12 is an isometric view of an embodiment of the general uterine manipulator and associated system with additional fittings to enable performance of a total laparoscopic hysterectomy; and, FIG. 13a is a side view of a cervical funnel incorporated in an embodiment of the general uterine manipulator shown in FIGS. 1a and 1b;

FIG. 13b is a longitudinal section view of the cervical funnel;

FIG. 13c is an end view of the cervical funnel shown in FIGS. 13a and 13b;

FIG. 14b is a section view of the vaginal plug shown in FIG. 14a; and,

DETAILED DESCRIPTION OF THE PREFERRED EMBODIMENT

Figure 9C:
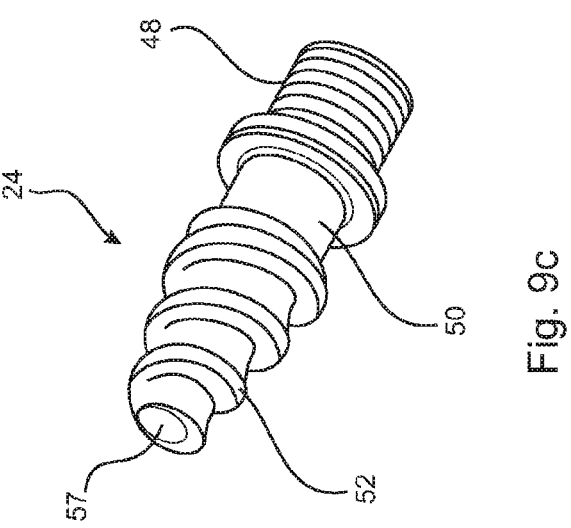
FIG. 9c is an isometric representation of the second fitting.

Embodiments of the general uterine manipulator and associated system provide a multipurpose manipulator that may be used for a variety of procedures by interchanging particular fittings of the manipulator. With particular reference to FIGS. 1a to 2, each embodiment of the general uterine manipulator 10 (hereinafter referred to in general as "manipulator 10") is based on or incorporates an elongated hollow tube 12 defining an internal passage 14. Tube 12 has opposite first and second ends 16 and 18 and a smooth continuous outer surface 20 of constant outer diameter. A first internal screw thread T1 is formed at the first end 16 and a second internal screw thread T2 is formed at the second end 18.

The versatility of the manipulator 10 and associated system arises from the ability to connect with a number of different fittings depending on the specific application at hand. FIGS. 1a and 1b illustrate a first fitting in the form of tail screw 22 and a second fitting in the form of a cervical screw 24. An inner manipulator rod 26 is also illustrated in FIGS. 1a and 1b which extends through the first fitting 22, tube 12, and second fitting 24.

One form of the first fitting 22 is shown in greater detail in FIGS. 3 to 5. In this embodiment the first fitting 22 comprises a threaded portion 28; an integral body portion 30; and, an internal axial hole 32. Threaded portion 28 is configured to engage screw thread T1 and is provided with a transverse slot 34 terminating prior to the body portion 30. Slot 34 in effect divides the threaded portion 28 into opposed clamp shells 36a and 36b (hereinafter referred to in general as "clamp shells 36"). Body portion 30 is in the general form of a cylinder with two flats 38a and 38b on opposed sides that assist in gripping of the fitting 22. Axial hole 32 is of constant diameter for the length of the fitting 22 except for a counter sink 40 at a distal end of fitting 22.

Threaded portion 28 is slightly flared outwardly so as it is screwed into screw thread T1 at end 16, the clamp shells 36 move toward each other. When an inner manipulator rod 26 is used in the manipulator 10 this results in a clamping action on the rod providing resistance to movement of the rod 26 so as to hold it at a desired rotational and translational position. Unscrewing of the portion 28 releases or reduces this resistance to enable adjustment of the position and orientation of the rod 26. Thus the first fitting can be considered in this embodiment as incorporating or comprising a resistance mechanism which substantially maintains the position of the rod 26 until moved or adjusted by a surgeon or other user.

FIGS. 6 to 8 depict an alternate form of the first fitting denoted as 22'. Features of the fitting 22' which are of the same or similar configuration or function as those of fitting 22 are denoted with the same reference numbers but with the addition of the prime (') symbol. Fitting 22' comprises a threaded portion 28', body 30', an inner axial hole 32' with counter sink 40' at a distal end, and opposed flats 38'a and 38'b formed on body portion 30'. Fitting 22' differs from fitting 22 by the omission of slot 34, the inclusion of a hydrotubation port 42, and a re-configuring of the axial hole 32'. With particular reference to FIG. 7 it can be seen that the axial hole 32' has a first length 44 and a contiguous second length 46. The first length 44 extends from the threaded portion 28' for a majority of the axial length of fitting 22'. The second length 46 extends between and joins the counter sink 40' to the first length 44. The inner diameter of the first length 44 is greater than the inner diameter of second length 46'. Further, the inner diameter of second length 46 is dimensioned to be slightly greater than an outer diameter of the inner manipulator rod 26 forming a close fit but enabling the rod 26 to pass through the axial hole 32'.

Hydrotubation port 42 is formed in the body 30' at a location where it communicates with the first length 44. The thread on threaded portion 28' is arranged to engage with the thread T1 at end 16. In the event that for example the manipulator 10 is being used in a gynaecological application and it is desired to inject a liquid such as a dye to assist in the visualisation of tissue the dye may be injected through the hydrotubation port 42. The dye then flows through the internal passage 14 and from an opposite end of second fitting 24 attached to end 18. In this regard in the event that manipulator rod 26 is in use, a clearance exists between second fitting 24 and an outer surface of rod 26 to allow the flow of dye or other fluid. Further, the close fitting between the rod 26 and second length 46 of axial hole 32' substantially prevents any back leakage of the dye. Alternately and/or in addition if desired, a rubber grommet seal (not shown) may be provided in the second length 46 to further minimize back leakage of dye or other liquid injected through the hydrotubation port 42.

As the fitting 22' does not have the clamping shells 36 of fitting 22 it is unable to clamp inner manipulation rod 26. However in embodiments of the manipulator 10, the inner manipulator rod 26 can be bent to varying degrees intermediate of its length so that the rod 26 bears against an inside surface of tube 12 to provide resistance to both axial and rotational motion when fitting 22' is used. This still allows the rod 26 to substantially maintain its position until moved or adjusted manipulated by a surgeon or other user. Thus the intermediate bend in the rod 26 can be equated with or considered to be another or alternate form of resistance mechanism which substantially maintains the position of the rod 26 until moved or adjusted by a surgeon or other user.

Figure 9A:
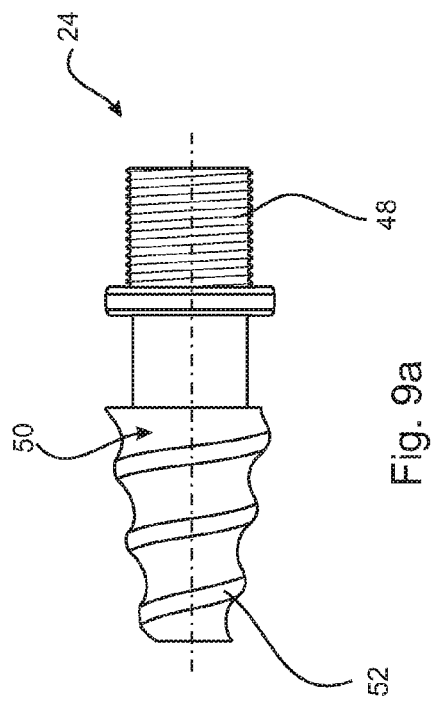
FIG. 9a is a side view of a second fitting incorporated in the general uterine manipulator shown in FIGS. 1a and 1b.
Figure 9B:
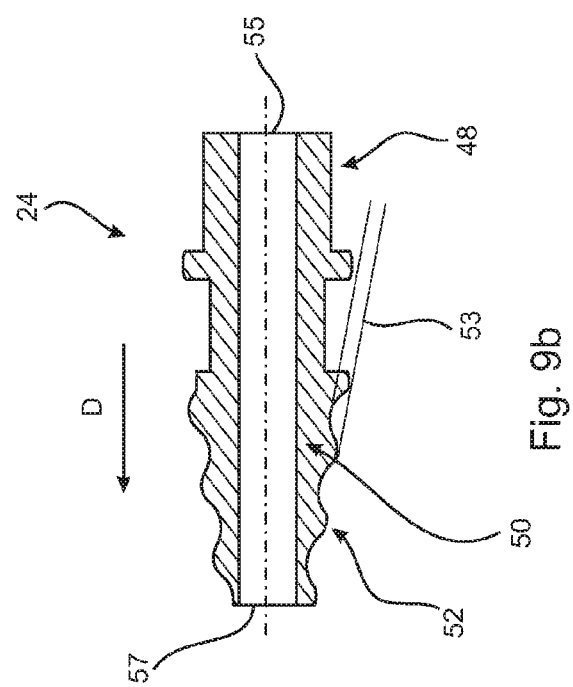

The second fitting 24 of FIGS. 1a and 1b is shown in greater detail in FIGS. 9a, 9b and 9c. The fitting 24 comprises a threaded portion 48 configured to engage thread T2, and an integral body portion 50. Body portion 50 is of a frusto-conical shape with a decreasing outer diameter in a taper direction D being away from threaded portion 48. A coarse screw thread 52 is formed about the conically shaped body portion 50. The crest of thread 52 has a flattened surface orientated so that a line 53 on the surface of the crest is inclined parallel with a central axis 55 of second portion 24. An axial through hole 57 is also formed through second portion 24. This allows for the passage of the inner manipulator rod 26 and/or other instruments as well as fluids including saline, dye, and air. In this embodiment of the manipulator 10, second fitting 24 is a cervical screw which is configured to screw into the cervix forming an attachment point as well as a seal.

However, alternate forms of second fittings may be incorporated in the manipulator 10. FIGS. 10a-10d illustrate an alternate second fitting 24a. Fitting 24a is in the form of a hollow probe having a threaded portion 48a and a body portion 50a. Threaded portion 48a has a thread configured to engage with thread T2. Body portion 50a is in the form of a tubular member which is open at its distal end 56 and is closed at an end 58 near threaded portion 48a to define or otherwise form a cavity 60. Distal end 56 is formed with a chamfer or bevel 62 to assist in insertion of the fitting 24a into a body cavity such as a vagina or rectum. Fitting 24a may be used for example during a hysterectomy to maintain pneumoperitoneum after removal of the uterus. The cavity 60 also allows for collection of pelvic tissue and specimens from the abdominal and pelvic cavities. A lumen (i.e. through hole) 64 may be formed axially through a circumferential wall 66 of the body 50a. In one embodiment the lumen 64 may have an internal diameter of approximately 6 mm to enable the receipt of a 4 mm telescope to enable illumination and visualization of tissue in cavities. For example this may be used in pelvic floor operations where the vagina and rectum septum need to be dissected out. This reduces the possibility of a recto-vaginal fistula occurring.

It is envisaged that the fitting 24a may be made in a variety of different sizes and in particular different diameters. For example 40 mm outer diameter, 30 mm outer diameter, and 20 mm outer diameter.

Figure 11:
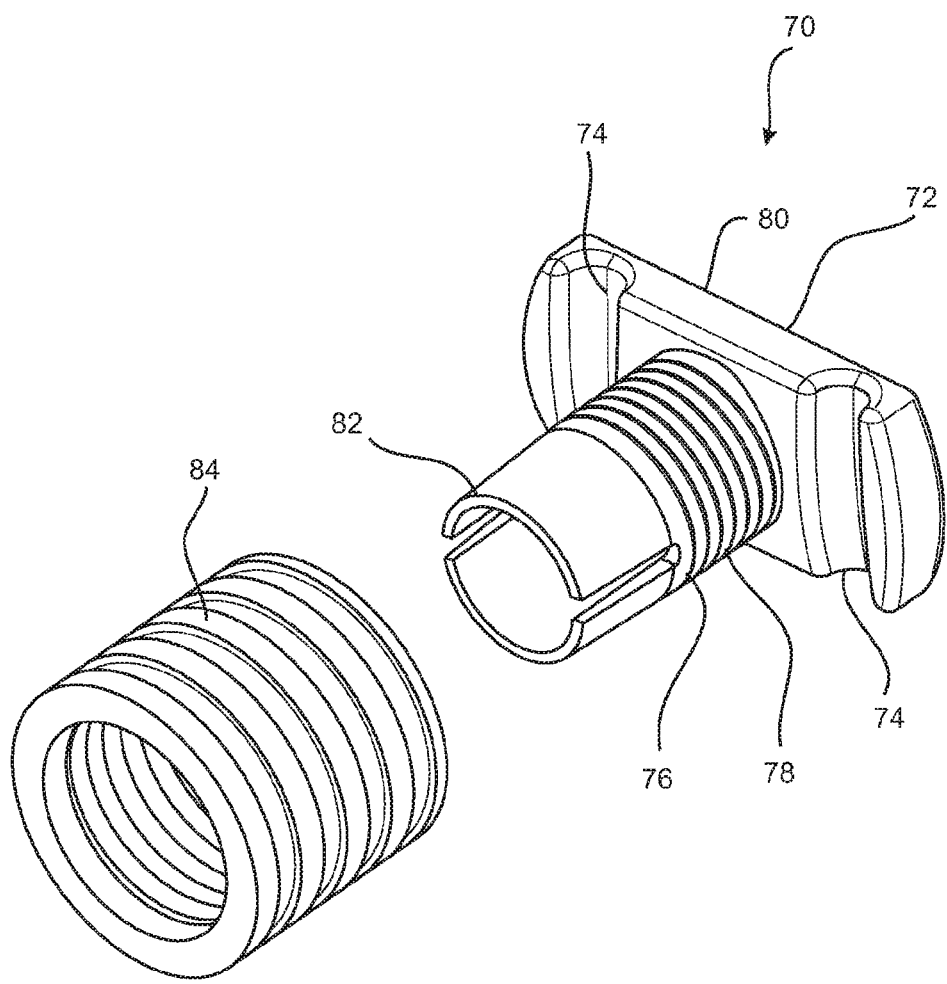
FIG. 11 is an isometric view of a forceps holder incorporated in the uterine manipulator.

FIG. 11 illustrates one form of a forceps holder 70 that may be incorporated in an embodiment of manipulator 10. The forceps holder 70 is configured to seat on the elongated hollow tube 12 and releasably lock at a desired location along the tube 12. Forceps holder 70 comprises a first component 72 that is able to slide over and along tube 12 and is provided with detents 74 for gripping a handle of the forceps. Two detents 74 are shown on opposite sides of a central boss 76. However in other configurations alternate numbers of detent 74 may be provided. The boss 76 is provided with a screw thread 78 extending from a cross piece 80 which contains the detent 74. Extending axially from the thread portion 78 is a split collar 82. The forceps holder 70 also includes a locking nut 84 that is able to screw onto the threaded portion 78 over the split collar 82 and act to clamp the collar 82 onto an outer surface of the tube 12 thereby releasably locking the holder 70 at an outside location along the tube 12. In one example, the forceps holder 70 may be used to hold valsellum forceps which in turn holds the manipulator 10 to the cervix making the manipulator self retaining.

With reference to FIGS. 12-14b, the manipulator 10 may also support a cervical funnel 90 and a plug 92. The cervical funnel 90 is formed as a unitary device comprising a tube 94 of constant inner and outer diameter and an integral conical portion 96 which increases in outer diameter in a direction away from first end 16 of tube 12. The conical portion is provided with a lip 98 that extends about a part of the circumference of conical portion 96 and is flared in a radial outward direction.

Plug 92 sits on the outside of funnel 90 and when used in gynaecological procedures forms a plug in the vagina. With reference to FIG. 12, it can be seen that the forceps holder 70 may also act as a positioning device for the funnel 90.

FIGS. 13a and 13b depict in greater detail the cervical funnel 90 incorporated in the manipulator 10 shown in FIG. 12. The lip 98 is flared outwardly by an angle of approximately 130°. In this embodiment the outermost edge of the lip 98 extends for an arc α of approximately 115° about the conical portion 96. An inside diameter of the tube 94 is arranged to be slightly greater than the outer diameter of the tube 12 to enable the cervical funnel 90 to be rotatably and linearly moveable with respect to the tube 12.

Figure 14B:
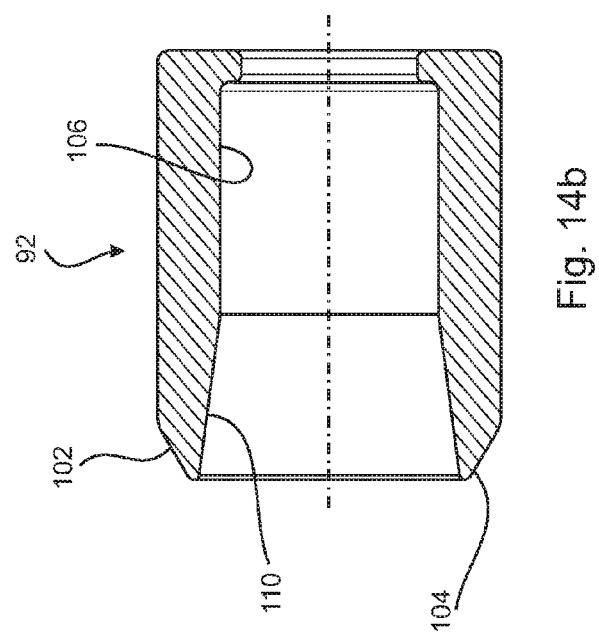
Figure 14A:
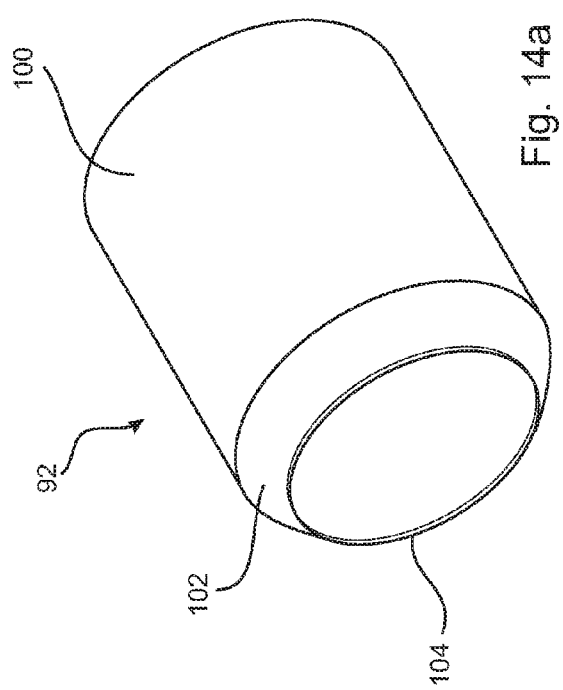
FIG. 14a is an isometric representation of a vaginal plug incorporated in an embodiment of the general uterine manipulator shown in FIGS. 1a and 1b.

FIGS. 14a and 14b depict in greater detail the vaginal plug 92 shown previously in FIG. 12. The plug 92 has a main body 100 formed of a constant outer diameter and a contiguous distal end portion 102 of progressively reducing outer diameter tapering to the distal end 104 of the plug 92. When the plug 92 is used with the manipulator 10, it is orientated so that the distal end portion 102 is directed toward the second fitting 24. An interior surface 106 of the plug 92 has a first portion 108 of constant inner diameter, and a contiguous second portion 110 of progressively increasing outer diameter. More particularly, the surface of the portion 110 is arranged to seat an exterior surface of the conical portion 96 of cervical funnel 90. Thus the increase in inner diameter of the surface of portion 110 is substantially the same as the angle of increasing diameter of the outer surface of conical portion 96.

Figure 15:
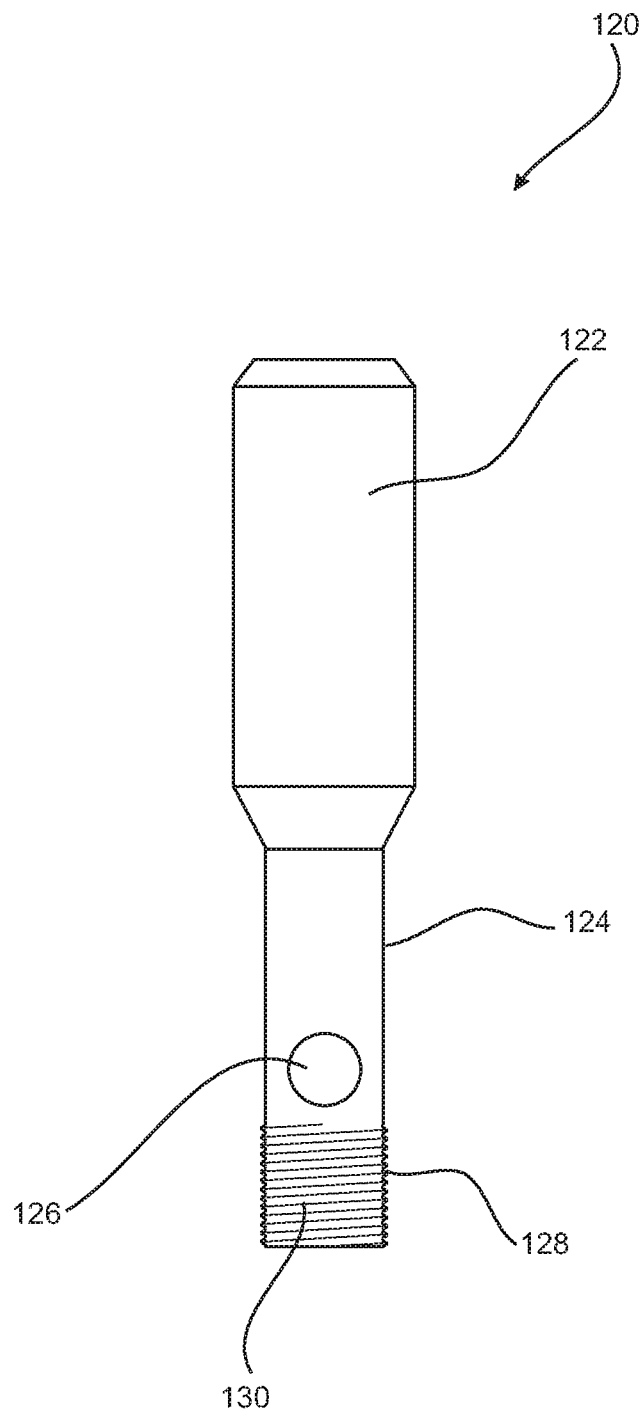
FIG. 15 is a side view of a manipulator handle which may be incorporated in an embodiment of the general uterine manipulator.

FIG. 15 depicts an optional handle 120 incorporated in embodiments of the manipulator 10. The handle 120 comprises a grip 122 and a contiguous extension 124. The extension 124 is provided with a through hole 126 and a screw thread 128. The screw thread 128 extends from approximately the location of the hole 126 to an end 130 of the handle 120. The through hole 126 is dimensioned to enable the tube 12 to pass there through either with a slight interference fit or a small clearance. Thus the handle 120 extends perpendicular to the tube 12. The screw thread 130 is configured to enable coupling with a nut such as a second locking nut 84. The locking nut when tightened on screw thread 128 can then act to clamp the handle 120 to the tube 12. The handle 120 can be applied to any portion of the tube 12 between the end fittings 22 and 24 which is not otherwise covered by other components such as the cervical funnel 90.

From the above description it will be recognised that dependant on the application at hand the manipulator may take many different forms owing the interchangability of first and second fittings and the ability to use additional components such as the rod 26, the forceps holder 70, cervical funnel 90 and the plug 92. It is envisaged that a general uterine manipulator system or kit may be provided to surgeons and doctors composed of all or at least a selection of the first and second fitting; together with other components such as the rod 26, forceps holder 70, cervical funnel 90 and the plug 92. In this way the surgeon or doctor will always have at hand various components to enable the performance of many different procedures.

Now that an embodiment of the invention has been described in detail it will be apparent to those skilled in the relevant arts that numerous modifications and variations may be made without departing from the basic inventive concepts. For example, in one embodiment, the hydrotubation port 42 is illustrated and described as being formed on the first fitting 22. However in an alternate embodiment, a hydrotubation port may be formed on the tube 12 at a location near first end 16 but beyond the screw thread T1. In one embodiment, the first and second fittings 22, 24 may be formed from a plastics material so as to be disposable after a single use while the elongated hollow tube 12 may be made from surgical grade stainless steel so as to be reusable. All such modifications and variations together with others that would be obvious to persons of ordinary skill in the art are deemed to be within the scope of the present invention the nature of which is to be determined from the above description and the appended claims.

What is claimed is:

1. A uterine manipulator system comprising:
a cervical funnel that is formed as a unitary device, the cervical funnel having a conical portion and a straight portion, the straight portion extending from a distal end of the conical portion, and the cervical funnel configured for insertion into and for contact with a vaginal cavity;
the straight portion having an integral lip extending circumferentially about the straight portion; and
the integral lip extending radially outward, the integral lip comprising a distal tip portion and first and second side portions, the distal tip portion having a straight surface extending in an arc between the first side portion and the second side portion, the first and second side portions tangentially aligned with the straight portion of the cervical funnel,
wherein a distal end of the integral lip defines a plane, and the straight surface is substantially perpendicular to the plane, at least at a midpoint of the integral lip.

2. The uterine manipulator system of claim 1, further comprising a manipulator configured to support the cervical funnel.

3. The uterine manipulator system of claim 2, wherein the cervical funnel is configured to be rotatably and linearly moveable with respect to the manipulator.

4. The uterine manipulator system of claim 2, the manipulator comprising:
an elongated hollow tube defining an internal passage and having opposite first and second ends;
a smooth continuous outer surface of constant outer diameter extending between the first and second ends; and,
internal first and second screw threads formed in the elongated hollow tube, the first screw thread being formed at the first end and the second screw thread being formed at the second end.

5. The uterine manipulator system of claim 4, the manipulator further comprising a first fitting having a screw thread arranged to engage the first screw thread, the first fitting also having an axial through hole and configured to receive an inner manipulator shaft.

6. The uterine manipulator system of claim 5, wherein the first fitting is configured to apply increasing clamping force on a received inner manipulator when the first fitting is screwed further into the first end.

7. The uterine manipulator system of claim 5, the manipulator further comprising a hydrotubation port formed in the first fitting and in fluid communication with the axial through hole wherein a fluid injected into or through the hydrotubation port is able to flow into the internal passage.

8. The uterine manipulator system of claim 7, wherein the axial through hole comprises a first length which opens onto an end of the first fitting distant the screw thread of the first fitting, and a second contiguous length wherein the first length has a first internal diameter and the second length has a second internal diameter which is greater than the first internal diameter; and wherein the hydrotubation port opens onto the second length of the axial through hole.

9. The uterine manipulator system of claim 5, the manipulator further comprising a second fitting having a threaded portion provided with a screw thread configured to engage the second internal thread on the elongated hollow tube and a body portion extending co-linearly from the threaded portion.

10. The uterine manipulator system of claim 9, wherein the body portion comprises a tubular member which is open at one end distal the threaded portion and is closed at an end near to the threaded portion to form a cavity.

11. The uterine manipulator system of claim 4, the manipulator further comprising a hydrotubation port in fluid communication with the internal passage wherein a fluid injected into or through the hydrotubation port is able to flow into the internal passage.

12. The uterine manipulator system of claim 11, wherein the hydrotubation port is formed in the elongated hollow tube at a location near the first end and beyond the first screw thread.

13. The uterine manipulator system of claim 1, wherein the lip comprises an outermost edge that forms an arc of about 115 degrees.

14. The uterine manipulator system of claim 1, further comprising a plug configured for insertion into a vagina, the plug configured to plug the vagina, the plug configured to be coupled to the cervical funnel, wherein the plug comprises a main cylindrical body having a constant outer diameter.

15. The uterine manipulator system of claim 14, wherein the plug comprises a distal end portion having a progressively reduced outer diameter tapering to the distal direction.

16. The uterine manipulator system of claim 14, wherein the plug comprises an interior surface having a first portion comprising a constant inner diameter.

17. The uterine manipulator system of claim 16, wherein the interior of the surface further comprises a second portion having a progressively increasing diameter.

18. The uterine manipulator system of claim 17, wherein the progressively increasing diameter of the second portion is substantially the same as an angle of the conical portion to enable the second portion to seat the conical portion.

19. A uterine manipulator system for insertion into a vaginal cavity, the uterine manipulator system comprising:
a cervical funnel comprising a first portion and a second portion, the first portion including an angled surface and the second portion including a straight surface that extends from a distal end of the first portion;

wherein the straight surface has a lip that extends distally from the straight surface and extends about the straight surface;

wherein the lip comprises a first side, a second side, and an edge extending between the first and second sides, wherein the edge has a substantially straight end extending between the first side and the second side, and wherein the first and second sides are tangentially aligned with the straight surface of the second portion; and wherein a distal end of the lip defines a plane, and the straight surface is substantially perpendicular to the plane, at least at a midpoint of the lip.

20. A method of using the uterine manipulator system of claim 1 to perform a laparoscopic surgery, the method comprising:

inserting the cervical funnel of the uterine manipulator system into the vaginal cavity;

rotating the cervical funnel to cause the integral lip to present a location for incision of vaginal tissue;

cutting the vaginal tissue at the presented location;

removing the cervical funnel from the vaginal cavity; and removing a uterus through the vaginal cavity.

* * * * *